United States Patent [19]

DeBaun et al.

[11] 3,947,475
[45] Mar. 30, 1976

[54] 5-FUROYL-2,2,4-TRIMETHYL-1,4-DIHYDRO-1H-1,5-BENZODIAZEPINE AS AN ANTI-INFLAMMATORY AGENT

[75] Inventors: Jack R. DeBaun, Sunnyvale; Ferenc M. Pallos, Walnut Creek; Don R. Baker, Orinda, all of Calif.

[73] Assignee: Stauffer Chemical Company, Westport, Conn.

[22] Filed: Apr. 28, 1975

[21] Appl. No.: 572,233

[52] U.S. Cl. ........ 260/347.3; 260/239 BD; 424/285
[51] Int. Cl.² ........................................ C07D 307/54

[58] Field of Search ............ 260/347.3, 239 BD, 80

[56] References Cited
OTHER PUBLICATIONS

Schulz et al., *Chem. Abst.*, Items 35626+35627, (1972).

*Primary Examiner*—Harry I. Moatz
*Attorney, Agent, or Firm*—Edwin H. Baker

[57] ABSTRACT

5-furoyl-2,2,4-trimethyl-1,4-dihydro-1H-1,5-benzodiazepine as an anti-inflammatory agent.

1 Claim, No Drawings

5-FUROYL-2,2,4-TRIMETHYL-1,4-DIHYDRO-1H-1,5-BENZODIAZEPINE AS AN ANTI-INFLAMMATORY AGENT

This invention relates to 5-furoyl-2,2,4-trimethyl-1,4-dihydro-1H-1,5-benzodiazepine which is useful as an anti-inflammatory agent.

The compound of this invention, 5-furoyl-2,2,4-trimethyl-1,4-dihydro-1H-1,5-benzodiazepine, is novel and has the following structural formula:

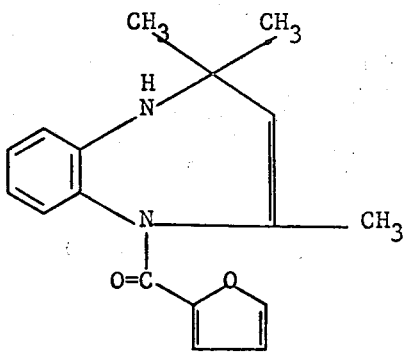

The compound of this invention can be prepared according to the teaching of the following examples.

EXAMPLE I

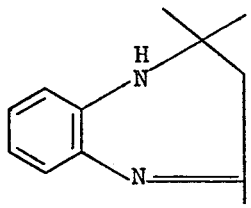

250 G (0.30 m) O-phenylene diamine, 2500 ml acetone and 2.5 g β-naphthalene sulfonic acid were mixed together and then refluxed on a steam bath for 17 hours, and then the solvent was vacuum stripped. Dark crystals formed. They were dissolved in 600 ml isopropyl alcohol and treated with 5 g Nuchar C-190A activated charcoal and filtered hot through Dicalite and allowed to cool. The resulting crystals were filtered off and worked with isopropyl alcohol and ether to yield 268 g of the desired product, m.p. 120°C.

EXAMPLE II

5-Furoyl-2,2,4-trimethyl-1,4-dihydro-1H-1,5-benzodiazepine

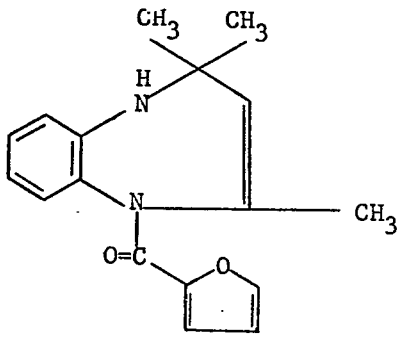

49 Ml (0.50 m) furoyl chloride was added dropwise to a mixture of 94.1 g (0.50 m) of the compound of Example I, 500 ml $CH_2Cl_2$ and 70.0 ml triethylamine over a period of 2 minutes. After standing for 2 days, a solid formed which was triethylamine hydrochloride. The mixture was washed with 500 ml water 2 times and 400 ml saturated $NaHCO_3$ solution, dried over $MgSO_4$ and vacuum evaporated to yield a solid which was washed with 200 ml ether. After air drying 103 g of the desired product, m.p. 120°C.

The product of Example II will hereinafter be called Compound Number 1.

ANTI-INFLAMMATORY SCREENING

The compounds of the present invention have pharmaceutical activity especially as anti-inflammatory agents. Anti-inflammatory activity is demonstrated by a test which involves the diminution of experimental edema induced in the hind paw of the rat by the injection of carrageenin.

Carrageenin injected into the foot of the rat produces an edematous condition which simulates part of the inflammatory process. Non-steroidal anti-inflammatory compounds inhibit the formation of this edema.

METHODS AND PROCEDURES

The procedures used for measuring the inhibition of carrageenin-induced edema is a standard procedure well known in the pharmaceutical art and is as follows:

Male rats (Long Evans Strain) weighing between 130–200 grams are used in this assay. Five rats each are used in the treatment groups and in the known standard control; whereas ten rats are used in the control edema group. Unless otherwise indicated, phenylbutazone is administered orally at 100 mg/kg to the standard control group. The edema control group is administered the vehicle which consists of 0.25% methylcellulose solution. All of the rats are fasted for at least 15 hours prior to the test. Water is available ad libitum. All of the experimental drugs are given orally and are dissolved or suspended in 0.25% methylcellulose solution. One hour after administration of the test compound, .05 ml of a 1% sterile solution of carrageenin is injected into the plantar tissues of the left hind paw of each rat. Three hours after carrageenin administration, the paw volumes of injected paws are then measured by means of a water displacement apparatus. The apparatus used is a modification of that described by Adamkiewicz et al., *Canadian Journal of Biochemistry and Physiology*, 33: 332, 1955. The amount of edema is calculated and the percent reduction of edema from control values is determined. The mean volume of edema, based on 50 determinations, is 1.25 cc with a standard deviation of 0.226 cc. A reduction in edema greater than 25% of the control value is considered significant. Based on 46 determinations, phenylbutazone produced a mean inhibition of edema of 43.8% with a standard deviation of 13.4%.

We have found that the compounds of this invention produce a significant inhibition of induced edema in rats at a dose rate of 200 mg/kg.

Table I shows the reduction in edema in the hind paw of the rat according to the above-described test procedure, at 200 mg/kg unless otherwise indicated.

TABLE I

| Percent Reduction in Edema at 200 mg/kg | |
|---|---|
| Compound Number | Percent Reduction of Induced Edema |
| 1 | 47 |

The compounds of the present invention, either alone or in the form of pharmaceutical composition may be administered to an animal subject in any of a number of forms and via any of several routes. Thus, the compounds or compositions thereof may be orally administered in the form of tablets, pills, capsules, or in the form of a suspension. The compounds may also be administered parenterally in the form of an injectable solution or suspension. The compounds or compositions thereof may also be administered topically, in the form of an ointment or rectally, in the form of a suppository.

When orally administering the compounds or compositions, use can be made of a tablet, pill or capsule consisting entirely of the desired compound, although ordinarily, a composition comprising an effective amount of the compound and varying amounts of one or more physiologically inert materials such as carriers, vehicles, binders and the like will be used. Additionally, the compounds may be orally administered in the form of a suspension thereof in a suitable vehicle such as a syrup.

When parenterally administering the compounds or compositions, use may be made of a parenteral solution or suspension of the compound in a suitable solvent or suspension medium.

The compounds of the present invention may also be administered rectally in the form of a suppository comprising an effective amount of the desired compound and a suitable vehicle such as petroleum jelly.

Finally, the compounds of the present invention may be applied topically in the form of an ointment, salve, cream or lotion comprising an effective amount of the desired compound and a suitable vehicle such as petroleum jelly, etc.

We claim:
1. 5-furoyl-2,2,4-trimethyl-1,4-dihydro-1H-1,5-benzodiazepine.

* * * * *